(12) United States Patent
Lopez Quintela et al.

(10) Patent No.: US 9,421,610 B2
(45) Date of Patent: *Aug. 23, 2016

(54) STABLE ATOMIC QUANTUM CLUSTERS, PRODUCTION METHOD THEREOF AND USE OF SAME

(75) Inventors: Manuel Arturo Lopez Quintela, Santiago de Compostela (ES); Jose Rivas Rey, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 2036 days.

This patent is subject to a terminal disclaimer.

(21) Appl. No.: 11/997,859

(22) PCT Filed: Jul. 28, 2006

(86) PCT No.: PCT/ES2006/070121
§ 371 (c)(1),
(2), (4) Date: Sep. 26, 2008

(87) PCT Pub. No.: WO2007/017550
PCT Pub. Date: Feb. 15, 2007

(65) Prior Publication Data
US 2009/0035852 A1    Feb. 5, 2009

(30) Foreign Application Priority Data
Aug. 3, 2005   (ES) .................................. 200502041

(51) Int. Cl.
*B22F 9/24*       (2006.01)
*C25C 5/02*       (2006.01)
*A61K 33/24*      (2006.01)
(Continued)

(52) U.S. Cl.
CPC ............. *B22F 1/0022* (2013.01); *A61K 33/24* (2013.01); *A61K 33/26* (2013.01); *A61K 33/28* (2013.01); *A61K 33/30* (2013.01); *A61K 33/34* (2013.01);
(Continued)

(58) Field of Classification Search
CPC ...... B22F 2998/00; B22F 1/0022; B22F 9/24; C25C 5/02; A61K 33/24; A61K 33/26; A61K 33/28; A61K 33/30; A61K 33/34; B82Y 15/00; B82Y 30/00
See application file for complete search history.

(56) References Cited

U.S. PATENT DOCUMENTS 5,417,958 A * 5/1995 Deutsch et al. .............. 424/9.42
5,814,370 A * 9/1998 Martino et al. .......... 427/213.35
(Continued)

FOREIGN PATENT DOCUMENTS

JP    2000-256707    9/2000
JP    2002-0888406   3/2002
(Continued)

OTHER PUBLICATIONS

Negishi et al. (JACS 2004, 126, 6518-6519).*
(Continued)

*Primary Examiner* — Ernst V Arnold
(74) *Attorney, Agent, or Firm* — Leason Ellis LLP

(57) ABSTRACT

Stable atomic quantum clusters, AQCs, characterized by being composed of at least 500 metal atoms, its production process characterized by having a kinetic control and by maintaining a low concentration of reagents in the reaction medium, as well as the uses of these clusters as sensors (fluorescent, magnetic or chemical), electrocatalysts and as cytostatics and/or cytotoxics.

17 Claims, 8 Drawing Sheets

(51) Int. Cl.
| | |
|---|---|
| A61K 33/26 | (2006.01) |
| A61K 33/28 | (2006.01) |
| A61K 33/30 | (2006.01) |
| A61K 33/34 | (2006.01) |
| B82Y 15/00 | (2011.01) |
| B82Y 30/00 | (2011.01) |
| B22F 1/00 | (2006.01) |

(52) U.S. Cl.
CPC . *B22F 9/24* (2013.01); *B82Y 15/00* (2013.01); *B82Y 30/00* (2013.01); *B22F 2998/00* (2013.01)

(56) References Cited

U.S. PATENT DOCUMENTS

| | | | |
|---|---|---|---|
| 6,494,932 B1 * | 12/2002 | Abercrombie | ............ 75/343 |
| 2002/0146748 A1 | 10/2002 | Sibley et al. | |
| 2005/0064618 A1 | 3/2005 | Brown et al. | |

FOREIGN PATENT DOCUMENTS

| | | |
|---|---|---|
| WO | 2004/003558 | 1/2004 |
| WO | 2004/014401 | 2/2004 |

OTHER PUBLICATIONS

Ion: [online] retrived on Mar. 30, 2011 from: http://www.merriam-webster.com/dictionary/ion; 2 pages.*
(Abstract: Becker et al. Computational Materials Science 1994, 2(3-4), 633-637) 2 pages.*
Kruckeber et al. (International Journal of Mass Spectrometry and Ion Processes 1996, 155, 141-148).*
Borisenko et al. Physics, chemistry and application of nanostructures, 2007, pp. 554 and 555). 2 pages.*
Dobbin et al. (Salts and their reactions, 1904, p. 178). 1 page.*
Kreibig et al., Handbook of Surfaces and Interfaces of Materials: Nanostructured materials, micelles and colloids 2001 Chapter 1; 85 pages).*
Cotton and Wilkinson Advanced Inorganic Chemistry 1980 4th Ed. pp. 1080-1112; 34 pages total.*
Schaaff and Whetten, "Giant Gold-Glutathione Cluster Compounds: Intense Optical Activity in Metal-Based Transitions", J. Phys. Chem. B 2000; 104: 2630-2641.
Barnett et al., "Structures and spectra of gold nanoclusters and quantom dot molecules", The European Physical Journal D 1999; 9: 95-104.
Crespo et al., "Permanent Magnetism, Magnetic Anisotropy, and Hysteresis of Thiol-Capped Gold Nanoparticles", Physical Review Letters 2004; 93 (8): 087204-1-087204-4.
Fotjik et al., "Electrochemistry of Mixed Metal Clusters in Aqueous Solution: Reduction of Ag+ by the Lead Atom", The Journal of Physical Chemistry 1992; 96 (21): 8203-8206.
Schmid, "Nanoclusters—Building Blocks for Future Nanoelectronic Devices?", Advanced Engineering Materials 2001; 3 (10): 737-743.
Petty et al., "DNA-Templated Ag Nanocluster Formation", J. Am. Chem. Soc. 2004; 126: 5207-5212.

Capadona et al., "Nanoparticle-Free Single Molecule Anti-Stokes Raman Spectroscopy", Physical Review Letters 2005; 94 (058301): 1-4.
Lee et al., "Voltammetry and Electron-Transfer Dynamics in a Molecular Melt of a 1.2 nm Metal Quantum Dot", J. Am. Chem. Soc. 2002; 125: 1182-1183.
Boyen et al. "Oxidation-Resistant Gold-55 Clusters", Science 2002; 297: 1533-1536.
Rao et al., "Size-Dependent Chemistry: Properties of Nanocrystals", Chem. Eur. J. 2002; 8 (1): 28-35.
Link et al., "Visibile to Infrared Luminescence from a 28-Atom Gold Cluster", J. Phys. Chem. B 2002; 106: 3410-3415.
Huang and Murray, "Visible Luminesence of Water-Soluble Monolayer-Protected Gold Clusters", J. Phys. Chem. B 2001; 105: 12498-12502.
Link et al., "Transition from nanoparticle to molecular behavior: a femtosecond transient absorption study of a size-selected 28 atom gold cluster", Chemical Physics Letters 2002; 356: 240-246.
Yang and Chen, "Surface Manipulation of the Electronic Energy of Subnanometer-Sized Gold Clusters: An Electrochemical and Spectroscopic Investigation", Nano Letters 2003; 3 (1): 75-79.
Negishi and Tsukuda, "Visible photoluminescence from nearly monodispersed Au12 clusters protected by meso-2,3-dimercaptosuccinic acid", Chemical Physics Letters 2004; 383: 161-165.
Lee et al., "Electrochemistry and Optical Absorbance and Luminescence of Molecule-like Au38 Nanoparticles", J. Am. Chem. Soc. 2003; 126: 6193-6199.
Zheng et al., "Highly Fluorescent, Water-Soluble, Size-Tunable Gold Quantum Dots", Physical Review Letters 2004; 93 (7): 077402-1-077402-4.
Negishi et al., "Glutathione-Protected Gold Clusters Revisited: Bridging the Gap between Gold (I)-Thiolate Complexes and Thiolate-Protected Gold Nanocrystals", J. Am. Chem. Soc. 2004; 127: 5261-5270.
Jimenez et al., "HPLC of Monolayer-Protected Gold Nanoclusters", Anal. Chem. 2003; 75: 199-206.
Rodriguez-Sanchez et al., "Kinetics and Mechanism of the Formation of Ag Nanoparticles by Electrochemical Techniques: A Plasmon and Cluster Time-Resolved Spectroscopic Study", J. Phys. Chem. B 2005; 109: 1183-1191.
Rodriguez-Sanchez et al., "Electrochemical Synthesis of Silver Nanoparticles", J. Phys. Chem. B 2000; 104: 9683-9688.
Roman-Velazquez et al., "Circular Dichroism Simulated Spectra of Chiral Gold Nanoclusters: A Dipole Approximation", The Journal of Physical Chemistry 2003; 107 (44): 12035-12038.
Garzon et al., "Chirality in bare and passivated gold nanoclusters", Physical Review B 2002; 66 (073403): 1-4.
Garcia-Bastida, et al. "Synthesis and structural characterization of Co immersed in Ag nanoparticles obtained by successive reactions in microemulsions" Science and Technology of Advance Materials. Jan. 7, 2005, vol. 6 pp. 411-419.
Tang, et al. "A simple solution-phase reduction method for the synthesis of shape-controlled platinum nanoparticles" Materials Letters. Apr. 5, 2005, vol. 59, pp. 1567-1570.
Rabin, I. et al., *Chemical Physics Letters*, 2000, pp. 59-64.
Belloni, J. et al., *New Journal of Chemistry*, 1998, vol. 22, No. 11, pp. 1239-1255.
B.S. Christopher Loo et al., *Technology in Cancer Research & Treatment*. 2004, vol. 3, pp. 33-40.

* cited by examiner

FIG 8
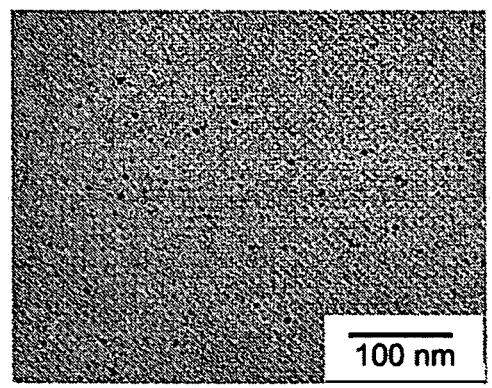
FIG 9
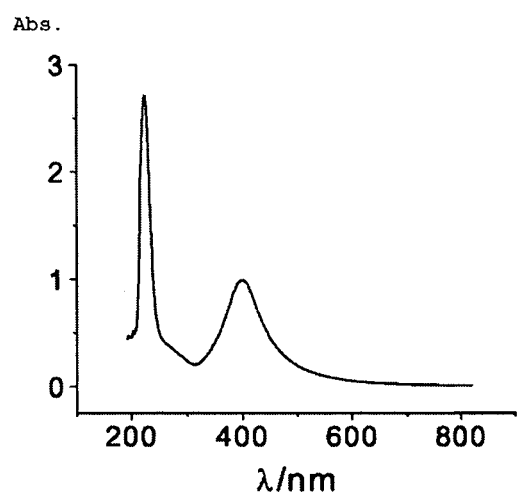
FIGURA 10
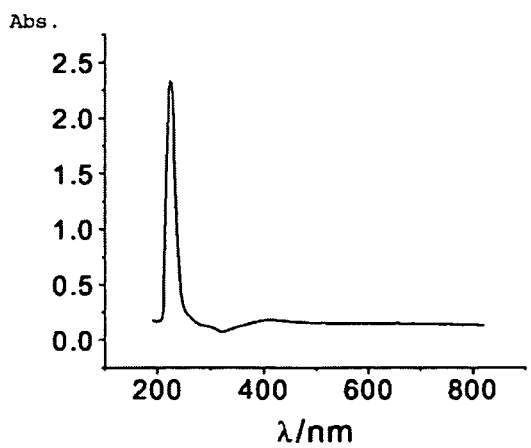

All the assays performed under nitrogene atmosfere
———— Vitreous carbon electrode
- - - - - - - Vitreous carbon electrode - in H2O2 - Curve A
-.-.-.-.-. Modified vitreo carbon electrode - in H2O2 - Curve B

STABLE ATOMIC QUANTUM CLUSTERS, PRODUCTION METHOD THEREOF AND USE OF SAME

CROSS-REFERENCE TO PRIOR APPLICATION

This is a U.S. National Phase application under 35 U.S.C. §371 of International Application No. PCT/ES2006/070121, filed on Jul. 28, 2006, and claims the benefit of Spanish Patent Application No. P200502041, filed on Aug. 3, 2005, both of which are incorporated herein by reference. The International Application was published in Spanish on Feb. 15, 2007 as WO 2007/017550.

The present invention relates to novel atomic quantum clusters (AQCs) of metal elements, characterized by their stability in solution, a process for their production by means of the reaction kinetic control and the uses of those AQCs as sensors (fluorescent, magnetic or chemical), electrocatalysts and as cytostatics and/or cytotoxics.

PRIOR ART

When materials are reduced to nano/subnano-metric sizes many of the properties change drastically and other new ones appear, as a consequence of the macroscopic-mesoscopic-atomic step. As an example, when the size of metal materials—such as Ag and Au— is reduced to a few atoms (<approx. 200-500 atoms) fluorescence appears [Zheng, J.; Zhang, C.; Dickson R. M. *Phys. Rev. Lett.* 2004, 93, 077402;], ferromagnetism [Crespo, P.; Litrán, R.; Rojas, T. C.; Multigner, M.; de la Fuente, J. M.; Sánchez-López, J. C.; García, M. A.; Hernando, A.; Penadés, S.; Fernández, A. *Phys. Rev. Lett.* 2004, 93, 087204], optical chirality [Schaaff, T. G.; Whetten, R. L. *J. Phys. Chem. B* 2000, 104, 2630], behaviour of redox-type charge [Lee, D.; Donkers, R. L.; DeSimone, J. M.; Murray, R. W. *J. Am. Chem. Soc.* 2003, 125, 1182], amplification of the Raman signal [Peyser-Capadona, L.; Zheng, J.; González, J. I.; Lee, T-H.; Patel, S. A.; Dickson, R. M. *Phys. Rev. Lett,* 2005, 94, 058301], etc.

All these new properties appear due to the spatial confinement of electrons which originates the quantum separation of the energy levels. In this way, these metal materials behave very differently to mass material. The fact that reducing the macroscopic material produces important changes in the properties of the materials is something already recognized as a characteristic of art in general. Thus, as an example, semiconductor materials—such as SCd, etc.—have quantum effects when their size is reduced to a few nanometers, which is used to syntonize their fluorescence at different wavelengths and, for this reason, they are currently called quantum dots, which aims to indicate the fact that the "quasi-punctual" quantum confinement which is originated in those semiconductor nanoparticles leads them to having different properties according to their size. In the case of metal materials, the drastic change in their properties occurs at lower sizes (less than a few hundred atoms), sizes corresponding to what is known as atomic clusters.

Due to the potential applications of the atomic quantum clusters especially in the field of biosensors [Peyser, L. A.; Vinson, A. E.; Bartko, A. P.; Dickson, R. M., *Science,* 2001, 291, 103], electrocatalysis [Boyen H-G. et al. *Science* 2002, 297, 1533], etc., a great interest has arisen for the development of simple synthesis methods which allow us to produce them in quantities which can be increased to large scale. And it is precisely there where the greatest problem lies for the application of AQCs. Until now, they have only been able to be produced through costly physical processes in gaseous phase [see for example, E. G. de Jongh (ed), *Physics and Chemistry of Metal Cluster Compounds. Model Systems for Small Metal Particles*, Series of Physical and Chemical Properties of Materials with Low-dimensional Structures, Kluwer Academi, Dordrecht, 1994], electrical or electrochemical processes but in very poor quantities of cluster mixtures of different sizes [Petty, J. T.; Zheng, J.; Hud, N. V.; Dickson, R. M. *J. Am. Chem. Soc.* 2004, 126, 5207.]. In this last case, the AQCs must then be purified by complex separation techniques (HPLC, gel electrophoresis, etc.) [Jiménez, V. L.; Leopold, M. C.; Mazzitelli, C.; Jorgenson, J. W.; Murray, R. W. *Anal. Chem.* 2003, 75, 199], so extremely small quantities of them are obtained, which makes it very difficult to study their properties and—more importantly—their application on a large scale. It should be highlighted that, in all cases, the clusters produced are either stabilized by protective molecules, solid or semi-solid matrices, etc. or their life time is too short to be able to be isolated [Rodriguez-Sanchez, M.; Rodriguez, M. J.; Blanco, M. C.; Rivas, J.; López-Quintela, M. A. *J. Phys. Chem. B,* 2005, 109, 1183], To date, the preparation methods of clusters/nanoparticles are based on the theory of nucleation-growth; these try to produce a very high number of nuclei in a very short time ("nuclei explosion"), for which purpose we try to accelerate the reaction speed to the maximum [Sugimoto, T *Monodisperse Particles* (Elsevier, New York, 2001)]. This is, for example, what is done in the well-known Brust method [Brust, M.; Walker, M.; Bethell, D.; Schiffrin, D. J.; Whyman, R. *J. Chem. Soc., Chem. Commun.* 1994, 801] to generate monodisperse gold nanoparticles.

The theory of nucleation-growth is a classic thermodynamic theory which is based on the fact that the formation of a new phase (solid in this case) within a liquid (the starting solution with the reagents) always implies the appearance of an interface and, therefore, requires an additional interfacial energy (called Laplace energy), given by the multiplication of the interfacial tension of the solid formed by the interfacial area formed. This energy means the particles which are smaller in size than the critical one are not stable and redissolve in the reaction medium. According to this theory only the particles with a size over the critical one are capable of creating and forming the solid particles finally produced.

Although it is not discarded that this form of thermodynamic reasoning is valid in certain circumstances, mainly for the preparation of metal particles with sizes over 1-5 nm, nevertheless, that approach is not suitable for the preparation of AQCs or atomic clusters, since in this case it does not make any sense to talk about classical thermodynamic concepts such as: Laplace pressure, critical nucleus, etc., thus it makes no sense to speak of cluster resolutions with sizes less that the critical one.

From the theoretical point of view, it has been predicted for some time now that the stability of the atomic clusters would be determined by other factors, from which the effect of electronic and/or atomic layers plays a fundamental role [(a) Kreibig, U.; Vollmer, M. *Optical Properties of Metal Clusters* (Springer-Verlag, Berlin, 1995); (b) Lee, H. M.; Ge, M.; Sahu, B. R.; Tarakeshwar, P.; Kim, K. S. *J. Phys. Chem. B* 2003, 107, 9994]. Thus, for isolated atoms, according to the "jellium" model [*Metal Clusters*, edited by W. Ekardt (Wiley, New York, 1999)], the clusters of 2, 8, 18, . . . atoms would be the most stable as they have complete electronic layers. On the other hand, taking into consideration the atomic symmetry, isolated clusters with m-Dh symmetry [Barnett, R. N.; Cleveland, C. L.; Häkkinen, H.; Luedke, W. D.; Yannouleas, C.; Landman, U. *Eur. Phys. J. D* 1999, 9, 95] would present greater stability for 38, 75, 101, 146, . . . atoms; whilst isolated clusters with fcc symmetry [Schmid, G. *Chem. Rev.* 1992, 92, 1709] would have greater stability for 13, 55, 147, 309, 561, ... atoms. It has only been possible to form these predictions in clusters with very short life produced in gaseous phase. The presence of molecules, chemical species, cavities and solid matrices may introduce an additional stability, as has been observed in different particular cases [see, for example Fojtik, A.; Henglein, A.; Jana, E. *J. Phys. Chem.* 1992, 96, 8203].

It is convenient to indicate that, although there are some specific processes to produce clusters of a particular size and for a certain metal, such as, for example those listed in patent WO2004/003558 to produce clusters of Au, Ag, Cu or metals of the platinum group formed by 227 metal atoms, or those described by G. Schmid [G. Schmid, Adv. Eng. Mat. 2001, 3, 737] for the preparation of $Au_{55}(PPh_3)_{12}Cl_6$, nevertheless, those clusters are only stable in the presence of stabilizing agents.

EXPLANATION OF THE INVENTION

The process object of the present invention has the purpose of the easy and quantitative production of AQCs (atomic quantum clusters of metal elements), stable, functionalized and of controlled sizes, so that it is easy and possible to scale the industrial production of this type of nano/subnano-materials.

Hereinafter, we will call the nano/subnanometric particles formed by metal elements, $M_n$, wherein M represents any metal, with n less than (<) 500 atoms, i.e. with a size less than 2 nm, as atomic quantum clusters and we will represent them by the acronym AQC.

It should be highlighted that, although the present patent of invention only relates to materials formed by elements commonly called metal, nevertheless many of them, due to the quantum confinement we have referred to and the consequent separation of the energy levels, may not have a metal but semiconductor or insulating character, depending on their size and on the ligands the AQCs are bound to directly.

According to a first aspect of the present invention, isolated and stable atomic quantum clusters (AQCs) are provided, characterized by being composed of less than 500 metal atoms (Mn, n<500, size<2 nm), preferably AQCs composed of less than 200 metal atoms (Mn, n<200, size<1.9 nm), more preferably AQCs of sizes less than 1 nm, even more preferably AQCs of between more than 2 and less than 27 metal atoms (Mn, 2<n<27, i.e. of between approximately 0.4 nm and 0.9 nm in size) and even more preferably AQCs formed by between 2 and 5 metal atoms and more particularly of 2 or 3 atoms (which corresponds with a size between 0.4 and 0.5 nm).

In the present invention, stable AQCs are understood as those groupings of atoms which maintain the number of atoms and, therefore, their properties, over time, so that they can be isolated and manipulated like any other chemical compound.

These AQCs are conserved for hours, even days, without the need of an external stabilizer.

In a preferred embodiment, the metals where those AQCs are formed from are selected from Au, Ag, Co, Cu, Pt, Fe, Cr, Pd, Ni, Rh, Pb or their bi and multimetal combinations. Preferably the metals of the AQCs are selected from Au and Ag or their bimetal combinations, because of the fascinating properties presented by some specific clusters of these metals, among which we can quote: catalysis, cytostatic properties, etc., which we will refer to later.

In another aspect of the present invention a process is provided for the preparation of those AQCs. That process consists of a reduction of the metal salt or ion (or metal salts or ions), and it is characterized by a kinetic control so that the reduction of the metal salt or ion (metal salts or ions) is slowly produced, simultaneously maintaining a small rate constant and a low concentration of reagents.

In the present invention, low concentration and small rate constant are understood as those values which lead the system through the minimum potential energy of the corresponding reaction coordinate. For practical purposes, low concentrations are understood as concentrations of the metal ion and/or reducer (if applicable) lower than a concentration of $10^{-3}$ M; and by small rate constants to those corresponding to semi-reaction life times over 1 second.

Therefore, the process consists, at minimum, of the following steps:

a. a kinetic control for the slow reduction, and b. maintaining a low concentration of reagents in the reaction medium.

Until now, the preparation methods of clusters/nanoparticles has been based on the theory of nucleation-growth. According to this theory, it is necessary that the nanoparticles/clusters production reaction is very fast in order to achieve a large quantity of nuclei. Once the nucleation has occurred, the nuclei all grow in unison and, in that way, nanoparticles of very monodisperse sizes are achieved.

Although the thermodynamic theory of nucleation-growth has had great success in explaining the preparation of monodisperse particles of micro and sub-micrometric sizes, nevertheless, the question is raised of up to what point the formation of an atomic quantum cluster of 3 or 4 atoms by chemical reaction in solution (for example, by reduction of a salt of the corresponding metal ion to be reduced) can be considered as a new phase. Indeed, the formation of a metal cluster of a few atoms by chemical reaction in solution is more similar to the innumerable examples that exist of formation of inorganic/organometallic chemical complexes (or also to the formation of polymers) from their reagents and, nevertheless, in all those cases the inorganic complex (or the polymer, provided that its molecular weight is not too high) is not associated with the formation of a new thermodynamic phase, but with the formation of a new "molecular" chemical compound to which, therefore, a superficial Laplace energy can be associated. In that case, the formation of the new compound is determined by the kinetics of the production process. And it is precisely the base on which the process proposed in the present invention is grounded: the use of kinetic control for the production of AQCs (atomic quantum clusters) of controlled size.

FIG. 1 shows a representative scheme of the variation of free energy throughout a reaction of metal formation in solution, from their metal ions. The reagents represent any metal ion in the presence of a reducer (or of a cathode where the reduction of the corresponding metal ion takes place). The reaction starts with the formation of an AQC of 1 atom ($M_1$), then two ($M_2$), etc. until, finally, solid particles of the reduced metal material (P) are produced. The figure represents the fact that as the AQC increases and approximates the size of a particle, P, (it is considered particle when the number of atoms of the atomic cluster is high, in the order of n greater than approximately 500 atoms (n> approx. 500 atoms), i.e. greater than approximately 2 nm, so that their properties are different from those of clusters of smaller size), so, the differences in energy between the different AQCs are less. It should be highlighted that the scheme is very general and does not indicate the fact generally found in practice that the potential troughs may be different (e.g. less for a smaller cluster than for another bigger one), as well as also that the activation energies may vary from some clusters to others. Furthermore, there may be other reaction pathways where a cluster with n atoms, $M_n$, can be associated to another with m atoms, $M_m$, to give a greater one with n+m atoms, $M_{n+m}$. It should also be highlighted that the differences in energy between troughs may be sufficiently small so there is an equilibrium between some of the clusters.

Therefore, the present invention is based on the idea that the kinetics play a decisive role in the formation of AQCs (atomic quantum clusters) and that, suitably controlling (slowing down) those kinetics the formation of specific AQCs can be controlled.

The formation of clusters is not limited to the type of metal element synthesized or the electrochemical method, so any other chemical method of reduction of metal salts in solution can be used for the production of these atomic clusters, as long as the reaction slows down sufficiently—as will be specified later—as to observe the evolution of the AQCs and stop the reaction (e.g. by cooling, dilution and/or fixation/separation of the clusters of the reaction medium) at the time that an AQC of a determined size is of interest. Precisely for this fact, the use of two-phase/bicomponent (water/organic compound) systems or two-phase/tricomponent systems (like microemulsions formed by water, organic compound and a detergent), wherein it is possible to have a very small concentration of reagents in the water/organic compound are particularly suitable for the preparation of clusters in macroscopically suitable quantities or the scaling of the production on industrial level.

This can be understood qualitatively supposing that a reaction is as if a wheel was slid over the curve of potential energy represented in FIG. 1. When a fast reaction is used, the energy transmitted to that wheel is so large that it exceeds the maximums between the different troughs and ends up dropping in the deeper troughs (i.e. quickly transforming in large-sized particles P—greater than 2-5 nm—). In contrast, the present invention, based on slowing down the reaction, involves communicating very little energy to the wheel. This, therefore, would initially fall in the first minimum ($M_1$ cluster) and only after an appreciable time will it successively drop in the following minimums corresponding to greater AQCs. That time/times the AQC takes to drop in the different minimums can be optimized to give time to separate the AQCs produced (e.g. by precipitation) or to stabilize them by introducing a chemical agent or stabilizing molecule in the reaction medium.

It is convenient to indicate that the initial introduction in the reaction medium of stabilizing agents can vary the minimum of the potential trough of some AQCs. Their initial introduction can be carried out to favour a determined type of AQCs and also to have greater time for the manipulation of the AQC before its definitive stabilization and functionalization. In any case, its introduction is not essential for the method proposed herein and which we will continue to describe below.

As has been previously highlighted, it is important in the present invention process 1) to slow down the reaction and 2) to maintain a low reagent concentration.

Thus, a preferred embodiment of the present invention, in order to slow down the reaction, is to use a mild reducer, which is selected from among the group which comprises sodium hypophosphite, amines, sugars, organic acids, polymers (such as polyvinylpyrrolidone), UV-VIS radiation, ultrasounds or electric current.

For the second point of maintaining low reagent concentrations, two forms can be used depending if the reaction medium is single or two-phase.

In the case of using a single-phase medium, the preferred form of proceeding is to generate the metal ion "in situ" in very low concentrations by the anodic solution (preferably a constant current) of an electrode of the corresponding metal.

The second option is to use a two-phase system (water/organic compound) in which the metal salt is dissolved in the water and a reducer which only dissolves in the organic compound is chosen (for example, but without being limited to, an amine, a thiol or an acid, of long chain hydrocarbon), so that the reaction only occurs in the interface and, therefore, with a very small local concentration of reagents.

In a preferred embodiment of the present invention, among others, cyclic, linear or branched saturated and unsaturated hydrocarbons are used as organic compounds, such as for example, but without being limited to, hexane, heptane, isooctane, cyclohexane; as well as also benzene or toluene.

In the case of the two-phase systems, in order to increase the reaction output the water-organic compound interface can be increased, using for this microemulsions formed by water, organic compound and a detergent which also allows the local concentration of reagents to be maintained very low inside the nanodrops of the microemulsion. In this case, as a detergent it is possible to use anionic detergents, such as aliphatic or aromatic sulfonates, for example, the derivatives of sulfocarboxylic acids; cationic detergents such as, for example, alkylammonium acetates or bromides; or non-ionic detergents such as, for example, polyoxyethylene derivatives.

As the reaction is made slow, following any of the described processes, the evolution of the clusters can be followed and, once the cluster of the desired size is achieved, it is possible to protect/stabilize the reaction medium by adding a stabilizing agent, which consists of a molecule which contains organic groups (such as thiols, sulfides, amines, acids, thioethers, phosphines or amino acids, etc.) in accordance with the metal wherefrom one wants to produce the cluster.

The separation of the cluster from the reaction medium can be carried out by precipitation, decreasing the temperature and/or adding a solvent incompatible with the cluster making use of the different solubility properties of the AQCs according to their size, as well as also by fixation, making use of their different affinity for those stabilizing groups.

For subsequent applications, the functionalized AQC could be produced. In that case the stabilizing agent has to be a molecule which must have, at least, two ends with different chemical groups: one end with one of the aforementioned groups to bond to the AQC and another with any other organic group (among which we can cite: double and triple bonds, alcoholic groups, acid groups or amine groups) for their subsequent interaction or bonding to other molecules or atoms for specific applications.

Thus, for example, functionalized AQCs can be prepared by adding dodecanethiol dissolved in pentane, observing the transfer of the clusters of the acetonitrile phase to the pentane phase. The introduction of a water-soluble thiol or thioether, such as for example, glutathione, thioglycol, thioacetic, etc. also allows their functionalization and transfer to water, so it is possible then to use an additional reaction to bond the AQCs thus functionalized to any another molecule, ion or substrate for the final applications required of the AQCs.

In order to identify the AQCs for their separation and isolation, the different properties of solubility and affinity can furthermore be used for the stabilizing groups the AQCs have according to their size—as just mentioned—, also the different optical, fluorescent, vibrational, redox, electrical and magnetic properties which these clusters have. Indeed, it has been observed that these AQCs have fluorescent properties. The fluorescence range varies between ultraviolet (for the smaller clusters, of 2-3 atoms), visible (for clusters between 4-10 atoms) and near infrared (for clusters over 10 atoms). It has also been observed that the fluorescence bands are very narrow, as shown in FIG. 17. Likewise, magnetic properties have been observed in these clusters. FIG. 18 shows an example of said properties. These properties can be used for the construction of fluorescent and magnetic sensors and biosensors.

Another aspect of the present invention discloses the use of the aforementioned AQCs as reducer chemical agents. Thus, it has been observed that the Au clusters are capable of reducing the methylene blue causing the disappearance of the band characteristic of the oxidised form (655 nm).

Another aspect of the present invention discloses the use of the aforementioned AQCs as electrocatalysts.

These clusters are very stable electrochemically so that the range of working potentials with dispersions of these clusters is limited by the values of the reduction and oxidation potentials of the medium wherein they are dispersed. Thus for example, the stability of the Ag clusters in TBAAc has been verified in the range (−3.V to +1.8V). Their high electrochemical stability makes them suitable for applications in various types of electrocatalysis reactions.

In a preferred embodiment, the AQCs show their electrocatalytic activity in reduction reactions, which include among others the reduction of the oxygen and/or hydrogen peroxide.

Stable dispersions of Ag, Au, Pt, Cu clusters, which have catalytic properties, have been synthesized. Those properties arise as a consequence of the enormous reducing power the metal clusters of a few $M_n$ atoms have (n<50-100).

The great electronic affinity of the clusters produces strong interactions with the electrons of other atoms even of the more electronegative ones such as, for example, halogens or oxygen, weakening the covalent bonds these atoms form in stable molecules. Thus, for example, the silver and gold clusters are capable of absorbing oxygen gas contributing to the dissociation of the molecules and, in consequence, lowering the necessary energy for their electroreduction. This fact is widely proven in example 3.

In another preferred embodiment, the AQCs have their electrocatalytic activity in alcoholic oxidation reactions.

Another aspect of the present invention provides the use of the aforementioned AQCs for the preparation of anti-cancer drugs for their cytostatic and cytotoxic properties.

These properties of the AQCs are here particularly demonstrated by in vitro tests performed with breast cells.

In the present invention, all the technical and scientific terms have the same meaning as that commonly understood by a person skilled in the art to which the invention belongs. Throughout the description and claims the word "comprises" and its variants do not aim to exclude other technical characteristics, components or steps. For people skilled in the art, other objectives, advantages and characteristics of the invention will be inferred in part from the description and in part from the practice of the invention. The following examples and drawings are provided by way of illustration and do not aim to be limitative of the present invention.

DESCRIPTION OF THE FIGURES

FIG. 8 shows an electronic microscopy photograph of the Ag AQCs synthesized according to example 2.

FIG. 9 This Figure shows the UV-vis spectrum of Ag AQCs 5 days after the synthesis.

FIG. 10 This Figure shows the UV-vis spectrum of Ag AQCs 13 days after the synthesis.

Triangles line: MeOH/NaOH (Pt modified)

Circles line: MeOH/NaOH (Pt unmodified)

Continuous line: NaOH (Pt unmodified)

Figure 15:
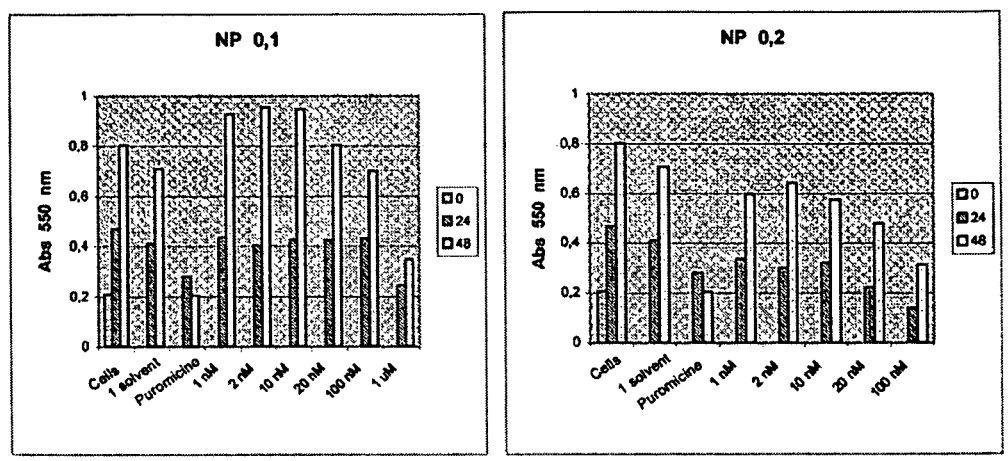

FIG. 15 This figure (NP 0.1 and NP 0.2) shows the absorbance (proportional to cell concentration) in accordance with the concentration of Ag clusters added. As reference, it shows the absorbance corresponding to the untreated cells. The results are compared with the effect of the pure solvent and the puromycin. The different bars show the results obtained after a different number of hours (0, 24 and 48 hours).

Figure 16:
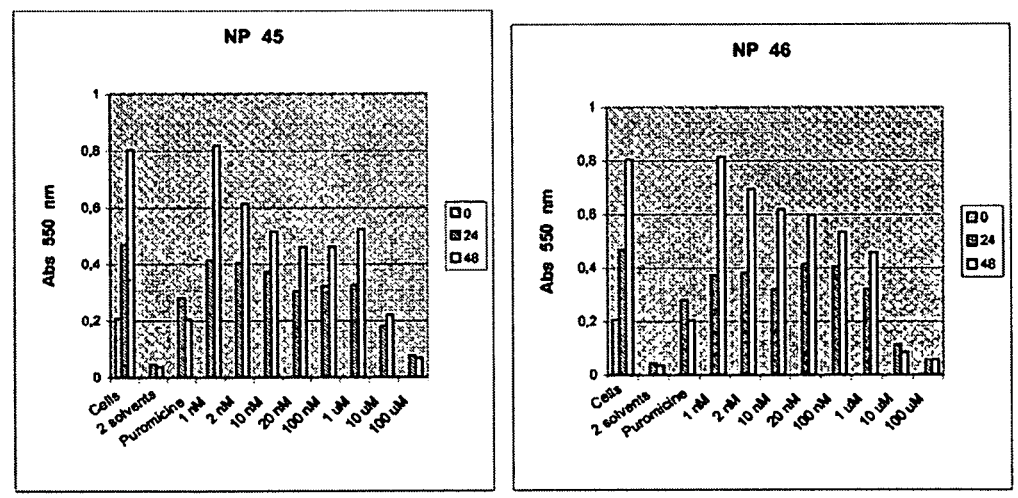

FIG. 16 This figure (NP 45 and NP 46) shows the absorbance (proportional to the cell concentration) in accordance with the concentration of Au clusters added. As reference the absorbance corresponding to the untreated cells is shown. The results are compared with the effect of the pure solvent and the puromycin. The different bars show the results obtained after different numbers of hours (0, 24 and 48 hours).

Figure 17:
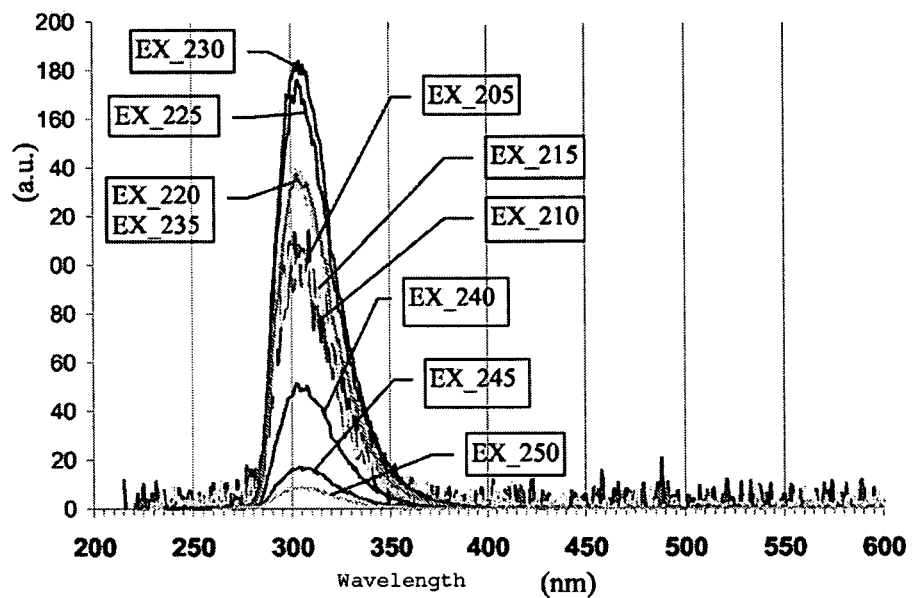

FIG. 17 Fluorescence spectrum of $Ag_n$ clusters (with n=2.3) for different excitation lengths.

Figure 18:
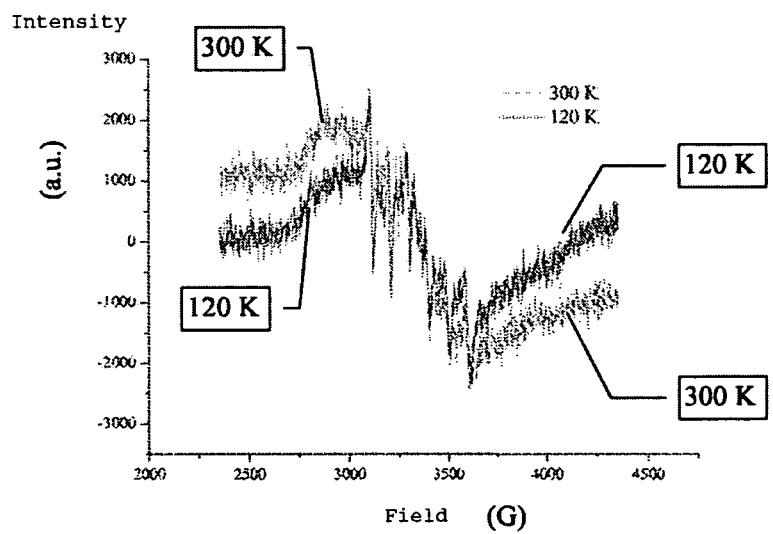

FIG. 18 EPR (Electric Paramagnetic Resonance) spectrum shows the paramagnetic resonance with hyperfine structure in $Ag_n$ clusters with n=5, at two different temperatures.

DETAILED EXPLANATION OF EMBODIMENTS

The invention will be illustrated below by tests performed by the inventors.

Example 1

Synthesis of Au AQCs

The synthesis of Au AQCs was carried out in an electrochemical cell, using galvanostatic potentiometry, applying a constant current density of 0 mA/cm$^2$ during 1000 s, in the following experimental conditions:

Working electrode: Pt (2.5 cm$^2$)
Counter electrode: Au (the metal wherefrom the AQCs are formed)
Reference electrode: Ag/AgCl
Electrolytic solution and stabilizing agent: 0.1 M in tetrabutyl ammonium bromide in acetonitrile.
Temperature: 25° C.
Inert Nitrogen atmosphere After the synthesis, the brown coloured AQCs initially obtained (AQCs of 1-2 atoms, as will be seen below) were transferred to an erlenmeyer, and it was observed that after 2 hours they took on a yellow colour, with a precipitate deposited in the bottom. The precipitation of the AQCs occurred due to the limited solubility thereof in the reaction medium.

These AQCs, predominantly of 3 atoms, separated by precipitation are much more stable that those of 1-2 atoms, (at least in the experimental conditions used), since, even without any additional protection, they remained stable for 5 months at an ambient temperature.

Once produced, the clusters can be functionalized. Thus, for example functionalized AQCs were prepared by adding dodecanethiol dissolved in pentane, observing the transfer of the clusters from the acetonitrile phase (which became transparent) to the pentane phase (which turned yellow).

Figure 1:
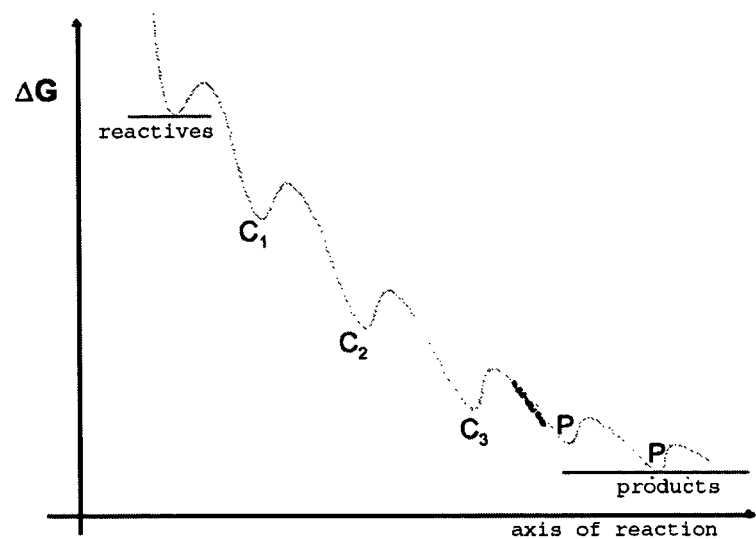
FIG. 1 shows a representative scheme of the variation of free energy throughout the reaction to form metals in solution, from their metal ions. The reagents represent any metal ion in the presence of a reducer (or of a cathode where the reduction of the corresponding metal ion takes places). $M_1$ relates to an AQC of 1 atom, $M_2$ of two atoms, etc. and P relates to the solid particles of the reduced metal material.
Figure 2:
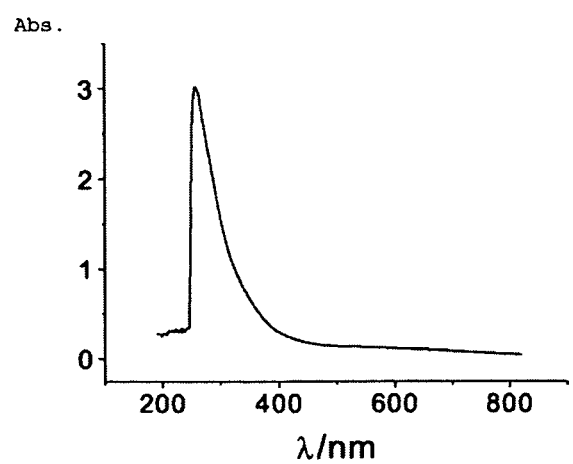
FIG. 2 shows the spectrum characteristic of the Au AQCs produced by precipitation and stabilized with dodecanethiol.

FIG. 2 shows the characteristic spectrum of the Au AQCs produced by precipitation and stabilized with dodecanethiol.

Figure 3:
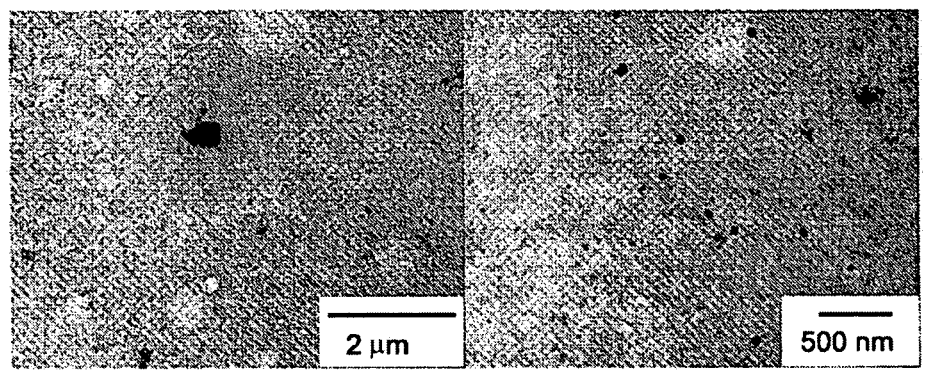
FIG. 3 shows an electronic transmission microscopy of groupings of the synthesized Au AQCs. It should be highlighted that the sizes observed with microscopy (very polydisperse and greater than approx. 1-2 nm) do not really correspond to Au particles but AQC groupings.
Figure 4:
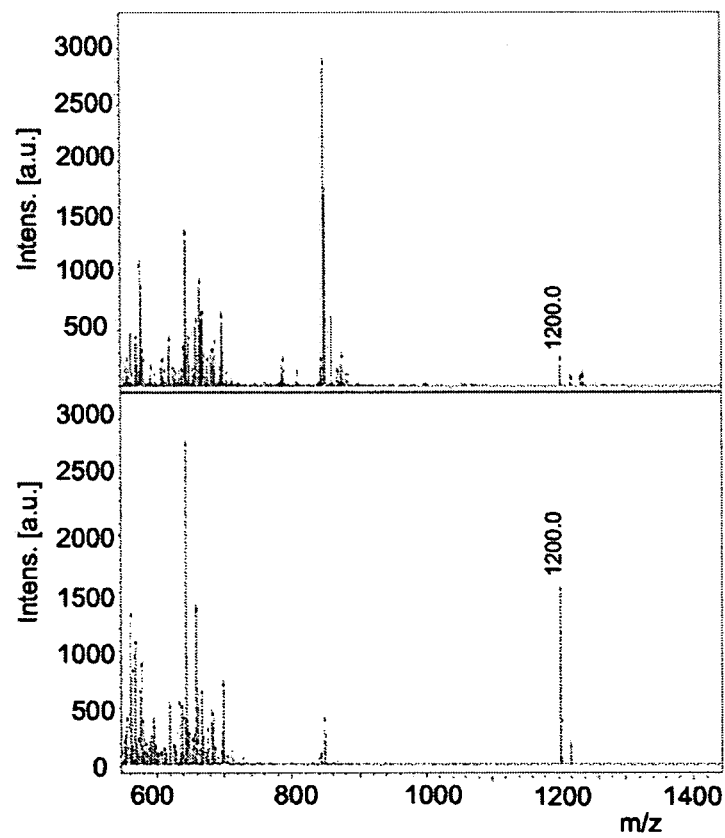
FIG. 4 shows the measurements made by mass electrospectrometry by flight time.

FIG. 3 shows an electronic transmission microscopy of groupings of the Au AQCs synthesized. It should be highlighted that the sizes observed in the microscopy (very polydisperse and over approx. 1-2 nm) do not actually correspond to Au particles but to AQCs groupings. Their small size makes their direct observation by electronic microscopy not possible and their presence can only be observed by the appearance of a blackish cloud as background of the microscope grille, together with the formation of groupings (clusters) of these AQCs of very different sizes, which were observed as blacker areas in the grille. The fact that the darker areas do not correspond to particles is also corroborated by the absence of the plasmonic band which should be visible in case they were not groupings of AQCs but nanometric-sized particles. In turn, measurements taken by mass spectrometry by flight time (FIG. 4) allowed us to clearly conclude that the clusters thus produced were predominantly formed by clusters of 3 atoms with the stoichiometric formula $Au_3(C_{12}H_{27}S)_3$ as demonstrated by the presence of the most important greater mass peak situated at 1200 uma. It is observed in this case that the $Au_3$ cluster is perfectly protected with the dodecanethiol used, where the dodecanethiol has lost the hydrogens of the SH group when bonding directly to the $Au_3$ cluster.

The fact that this cluster is $Au_3$ indicates that the clusters initially produced (brown coloured), precursors of the present 3-atom AQC, are formed by 2 atoms. It is observed that, even without protecting, those 2-atom clusters ($Au_2$) are stable in the reaction medium during approximately 2 hours. That time would be enough for their precipitation, isolation and subsequent protection and/or functionalization.

The unprotected Au $AQCs_3$ (in absence of thiol) were stable in those conditions for several months. After 5 months, the evolution of those AQCs towards the formation of other AQCs of greater size was observed, easily observable by the change in colour from yellow to red at simple sight. Those new AQCs of greater size precipitated (due to their lower solubility, since it decreases as the size of the AQC increases, due to the reduction in entropy of the mixture). Precipitation can also be favoured by decreasing the temperature. Thus, for example, the formation of an appreciable red precipitate was observed after one aliquot of the AQC solution on placing it at 0° C.

Figure 5:
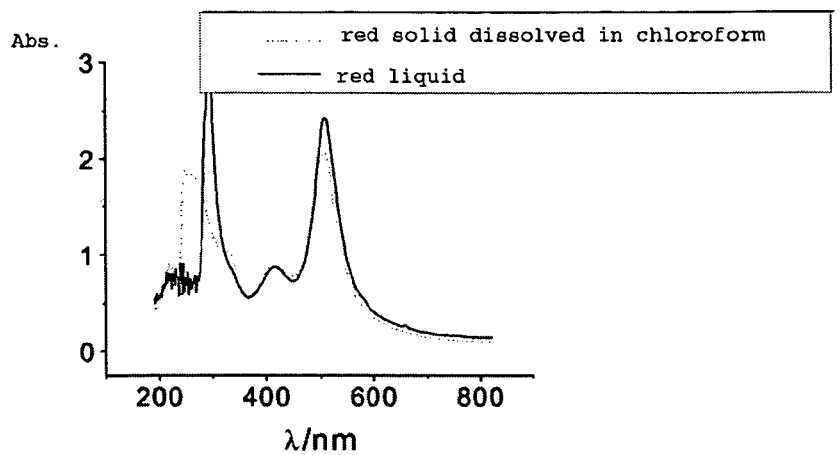
FIG. 5 shows the UV-VIS spectrum of the AQCs of greater size, both of those initially dispersed in the reaction liquid, and those produced by precipitation, protected by dodecanethiol, and redispersed in chloroform.
Figure 6:
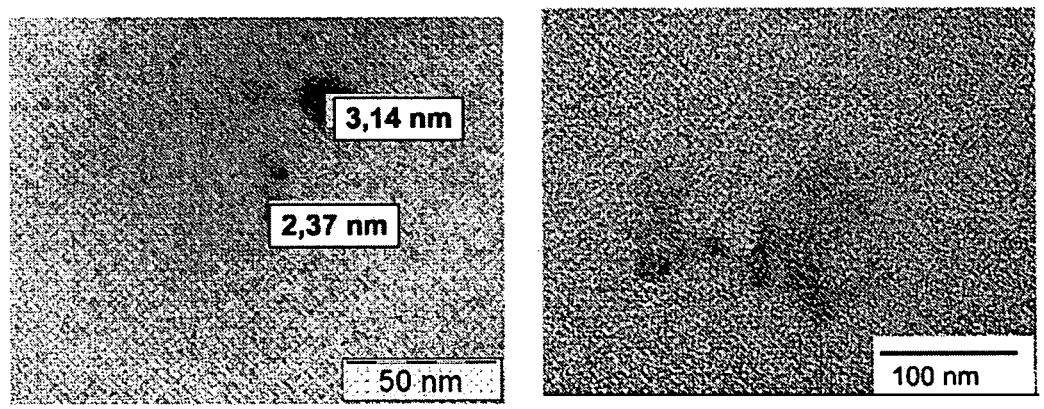
FIG. 6 shows an electronic microscopy photograph of the mixture of $Au_{12}$ and $Au_{21}$ AQCs which are formed by bonding of 4 and 7 clusters of $Au_3$.

FIG. 5 shows the UV-VIS spectrum of these last AQCs of greater size, not only of those initially dispersed in the reaction liquid, but also of those produced by precipitation, protected by dodecanethiol, and again redispersed in chloroform. The new bands which appear at 410 nm and 520 nm are indicative of the existence of mixtures of $Au_{12}$ and $Au_{21}$ AQCs, which are formed by bonding of 4 and 7 $Au_3$ clusters, respectively. FIG. 6 shows an electronic microscopy of these AQCs. Again, due to their small size, only a black background is observed, as well as darker stains in some parts of different sizes from the formation of denser groupings of these AQCs.

It should, finally, be indicated that the values of the experimental parameters indicated in this example, such as current density, type of cathode used, temperature, type and concentration of background electrolyte, are only indicative, as an example. Other current density values, elements used for the cathode, temperatures and types and concentrations of the background electrolyte, as well as protective agent, can also be used for the same purpose provided that a sufficiently small concentration of metal ions is maintained in the action medium so reaction occurs with the minimum potential energy.

Example 2

Synthesis of Ag AQCs

The synthesis of Ag AQCs was performed by using microemulsions of water/AOT/isooctane (AOT=aerosol OT=sodium bis 2 ethylhexyl sulfosuccinate) in the following experimental conditions:

$w_o$ ratio=[$H_2O$]/[AOT]=6
Solution of AOT in isooctane: 0.1M
Aqueous solution of $AgNO_3$: 0.1M
Aqueous solution of $NaH_2PO_2.H_2O$: 1M
Temperature: 25° C.

The synthesis was carried out by mixing two microemulsions, one with the reducer and another with the silver salt. The silver salt microemulsion was prepared by addition of 0.54 mL of the $AgNO_3$ aqueous solution to that of the AOT in isooctane, whilst that of the reducer was obtained by adding 0.54 mL of the aqueous solution of the sodium hypophospite reducer to that of the AOT in isooctane.

Figure 7:
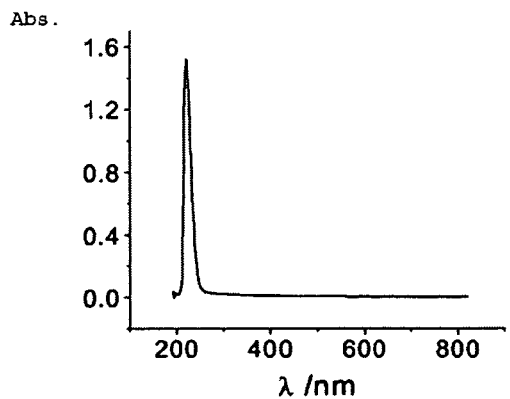
FIG. 7 shows the UV-VIS spectrum of the Ag AQCs synthesized according to example 2.

The addition of the $AgNO_3$ microemulsion to the reducer microemulsion was carried out in stirring conditions maintaining the dripping constant for 50 minutes. When that addition was finished, the mixture showed a yellow colour which gets a greater intensity as time passes, coming to be blackish due to the increase in AQC concentration, as can be deduced because when diluting the sample it gets a golden yellow colour again. FIG. 7 shows the UV-VIS spectrum of the Ag AQCs synthesized. The presence of a single band situated around 220 nm indicates that the size of these clusters is 2 atoms. FIG. 8 shows an electronic microscopy photograph of the Ag AQCs. The same occurs again with the Au AQCs: only a greyish stain is observed where some groupings of those AQCs are superimposed. The AQCs thus produced evolved after several hours with the formation of a new cluster of 4 atoms associated with the presence of a band situated around 260 nm.

Figure 11:
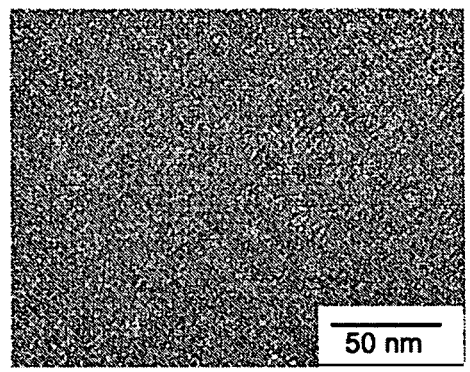
FIG. 11 This Figure shows an electronic microscopy photograph of the sample of Ag AQCs 13 days after the synthesis.

These $Ag_4$ clusters, without additional protection, were stable at ambient temperature, during at least 5 days (the stabilization is due, in this case, to the presence of the AOT surfactant), after which it evolves to the formation of an $Ag_{12}$ cluster as it is observed by the appearance of a new band situated around 400 nm, as shown in FIG. 9. In turn, these new $Ag_{12}$ clusters, without additional protection, remain stable during 12-13 days at ambient temperature. After that time, the $Ag_{12}$ clusters evolved to the formation of larger AQCs, which is observed by the colour change to greyish, which corresponds to the decrease in the band to 400 nm and the appearance of a broader band at greater lengths, as shown in FIG. 10. FIG. 11 shows a photograph of these last AQCs which, as can be observed, continue to be smaller than 1 nm, whereby only a grey stain is observed on the grille whereon they were deposited. As in the Au AQCs, if they did not stabilize and/or separated (e.g. by precipitation) the AQCs continued growing, reaching successively greater sizes. Finally, the size of nanoparticles was reached, clusters greater than approx. 500 atoms, finally observing the appearance of the plasmonic band which indicates the disappearance of the quantum effects of size and the formation of particle sizes over approx. 1-2 nm.

It should finally be indicated that in this example both experimental parameters used, and the type of amphiphile, the ratio of $[H_2O]/[detergent]$ concentrations=$w_o$, the volume of the dispersed phase, the organic solvent used, the temperature and concentration of the reagents, are only indicated as an example. Likewise, as commented in the description of the invention method, this method is not only restricted to single-metal clusters, also producing multimetal clusters following the same process. Thus, in the present example, if we substitute the aqueous solution of Ag in the initial reaction medium for a mixture of salts of Ag and Au and/or Cu and/or Co and/or Pt and/or Fe and/or Cr and/or Pd and/or Ni and/or Rh and/or Pb, we can obtain clusters formed by bi or multimetal combinations depending on the number and concentration of metal ions used.

Example 3

Electrocatalytic Activity of Metal Clusters in Oxygen Reduction

The electrocatalytic activity of metal clusters were verified comparing the voltammetric response in the oxygen reduction.

The following scheme illustrates the electrocatalytic activity of metal clusters in oxygen reduction:

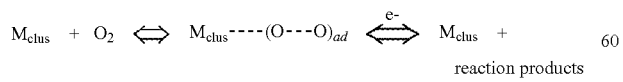

This reaction was carried out in acetonitrile solutions, using a polycrystalline Pt microelectrode (diameter=0.5 mm) as working electrode, a counter electrode of Pt and an Ag wire as pseudoreference (E=0.13V vsNHE).

Figure 12:
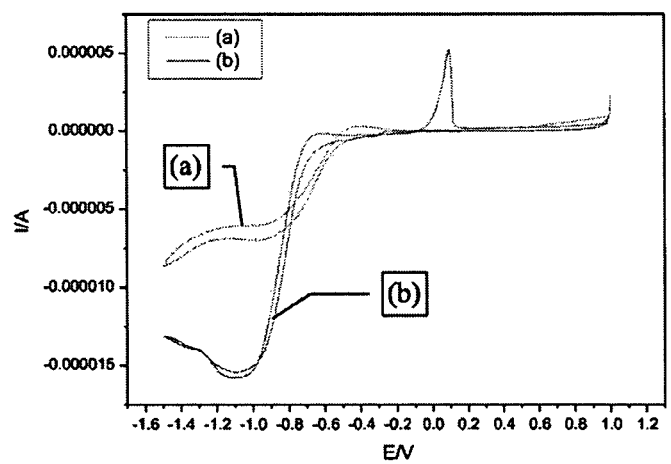
FIG. 12 Cyclic voltammetries ($E_{init}$=+1V) of 0.1M TBAAc, saturated with $O_2$. Working electrode: Pt polycrystalline, at 25° C., sweep rate 20 mV/s. (a) in absence, (b) in presence of clusters dispersed in the support electrolyte.

FIG. 12 shows the behaviour in cyclic voltammetry of the electroreduction of $O_2$ at saturation concentration, in 0.1M tetrabutyl ammonium acetate (TBAAc); in absence curve (a) and in presence curve (b), of silver clusters, $Ag_n$ (n=3, 4).

It was verified, as observed in FIG. 12, that, in the presence of clusters, a strong increase in the current around −0.7V was produced, which means that the Ag clusters used are more effective catalysts than the Pt, which is the most active catalyst known in oxygen reduction.

Example 4

Figure 13:
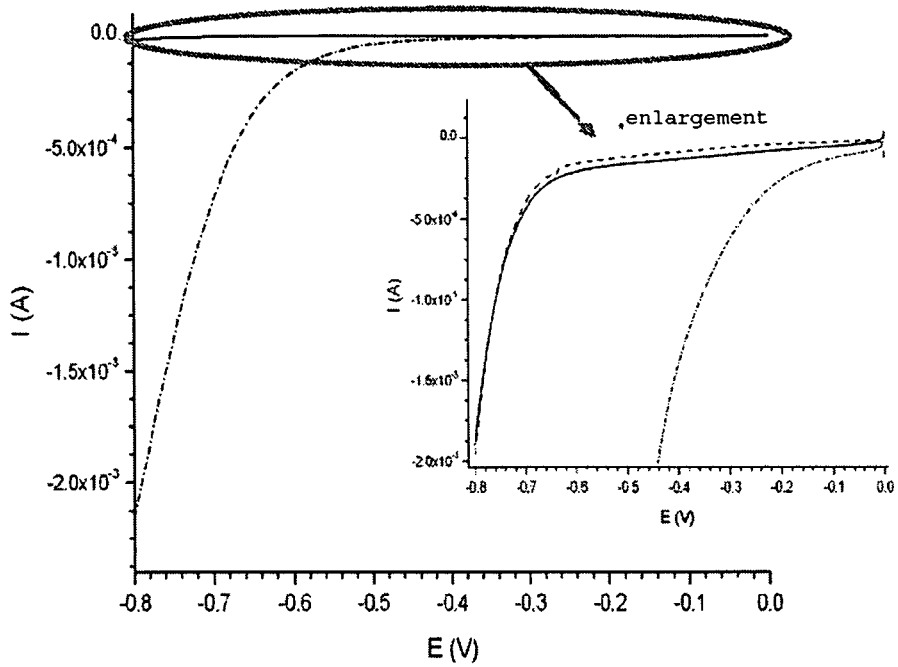
FIG. 13 Linear voltammetries in aqueous solutions of $H_2O_2$ in 0.5M perchloric acid. Working electrode: vitreous carbon (a) in absence, (b) in presence of clusters deposited on vitreous carbon. As a comparison a voltammetry of vitreous carbon in 0.5M perchloric acid is shown.

Electrocatalytic Activity of Metal Clusters in Hydrogen Peroxide, $H_2O_2$, Reduction The electrocatalytic effect of Ag clusters in $H_2O_2$ reduction has been verified taking measurements in free solutions of $O_2$ containing $H_2O_2$ as only species susceptible to reduction. FIG. 13 shows linear sweep voltammetries in aqueous solution containing 0.024M $H_2O_2$ and 0.5M $ClO_4H$. For the measurements, vitreous carbon (curve a) and vitreous carbon modified with silver clusters, Agn (n=3.4) (curve b) was used as working electrode. Pt wire was used as counter electrode. The potentials relate to an Ag/ClAg electrode (saturated). In that figure, after −0.15V, an increase in the $H_2O_2$ reduction current is observed in curve b (presence of Ag clusters) with respect to curve a (absence of clusters); in the enlargement, it can be observed that said increase is around 7% for E=−0.45V.

It was verified that these clusters have a catalytic activity greater than the Ag nanoparticles.

Example 5

Electrocatalytic Activity of Metal Clusters in Alcohol Oxidation

Figure 14:
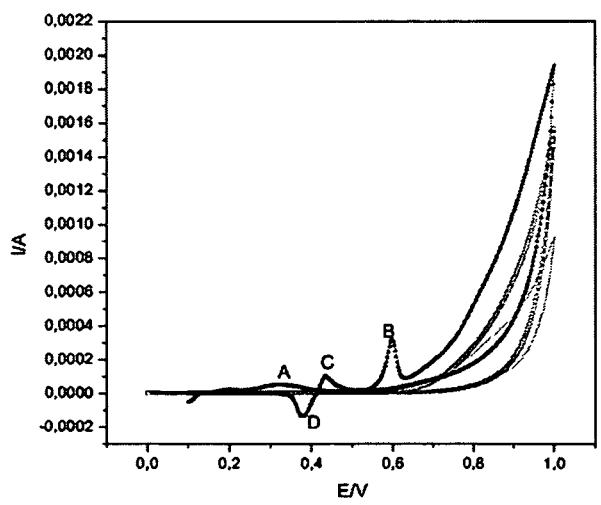
FIG. 14 Cyclic voltammetries ($E_{init}$=+0.1V) in an aqueous solution of 1M MeOH and 1M NaOH. Working electrode: Pt polycrystalline without and with clusters of Ag deposited. T=25° C., sweep rate 20 mV/s. As reference it is also shown the response of Pt in NaOH (continuous line)

The electrocatalytic activity of metal clusters was observed in alcohol oxidation, and more specifically the use of Ag clusters in methanol oxidation. That oxidation is produced in the range of 0V to +1V. To check that effect, the Ag clusters, dispersed in acetonitrile, were deposited on polycrystalline Pt. After checking the stability in the electrolytic medium, i.e. the absence of redox peaks, (up to E=+1.2V) of the clusters thus deposited, the modified electrode was transferred to an aqueous solution of 1M methanol containing 0.1M NaOH. The results can be observed in FIG. 14, where three oxidation peaks (A, B, C) were observed in the anode sweep, which correspond to the oxidation of the methanol on different sized clusters. The final increase in the oxidation current due to the presence of the clusters deposited on Pt (modified Pt) was also observed.

It is thus verified that the clusters are more effective catalysts in the oxidation of alcohols than the Pt.

Example 6

Toxicity Tests Via MTT

The toxicity of Au and Ag clusters on cultures of the MCF7 lines, of breast cancer, was evaluated, which were performed by cell viability studies with the methyl-thiazol-tetrazolium (MTT) salt.

$4 \times 10^3$ cells/well were seeded on 96-well plates in a total volume of 100 µL/well. The cells were stabilized for 24 hours, the initial medium was removed and it was replaced by 100

μL of medium with the treatments tested. After the exposure time, which varied between 24 and 48 hours, the MTT test was performed.

10 μL of MTT substrate were added and after 4 hours of incubation 100 μL/well of the lysis solution were added: 10% SDS in 10 mM HCl. After lysing the cells throughout the night, the absorbance was read at 550 nm in a Microplate Reader Model 550 (Bio-Rad).

Results:

6a) FIG. 15 shows the results on adding solutions of Ag clusters electrochemically prepared according to the first example and dispersed in water (samples NP 0.1 and NP 0.2 corresponding to clusters of 2-5 atoms and 6-15 atoms, respectively). The cytostatic effects of the clusters for concentrations over 1 μM can clearly be observed. These effects are comparable to those of a cytostatic habitually used such as Puromycin. It is further observed that the cytostatic effect is different according to the cluster type, as sample NP 0.2 is more effective, although in this case a certain cytotoxicity is observed, as can be seen due to the decrease in the number of initial cells (decrease in initial absorbance).

6b) FIG. 16 shows the results on adding solutions of Au clusters electrochemically prepared according to the first example (samples NP 45 and NP 46, corresponding to clusters of 2-5 atoms and 6-15 atoms, respectively). The cytostatic effects of the clusters for concentrations over 10 nM (sample NP45) and 100 nM (sample NP46) can clearly be observed. These effects are comparable to those of a cytostatic habitually used such as Puromycin. It is further observed that the cytostatic effect is different according to the cluster type, as sample NP46 is more effective, its cytotoxicity is also much greater, as can be seen due to the decrease in the number of initial cells (decrease in initial absorbance).

The invention claimed is:

1. Isolated stable atomic quantum clusters, AQCs, characterized in that they consist of more than 2 and less than 27 metal atoms and are not in gas phase.

2. AQCs according to claim 1, characterized in that they consist of between 2 and 5 metal atoms.

3. AQCs according to claim 1, where the metal is selected from the list which comprises Au, Ag, Cu, Pt, Fe, Cr, Pd, Ni, Rh, Pb, or any of their bi or multimetal combinations.

4. AQCs according to claim 1, where the metal is selected from the list which comprises Au, Ag, or any of their bimetal combinations.

5. Process for the production of the atomic quantum clusters (AQCs) of claim 1, by reduction of the metal atoms, characterized in that it:
   a. has a kinetic control for a slow reduction, and
   b. maintains a low concentration of reagents in the reaction medium.

6. Process according to claim 5, where mild reducers are used to produce the kinetic control.

7. Process according to claim 6, where the mild reducers are selected from the group which comprises hypophosphate, amines, sugars, thiols, organic acids, polymers, UV-vis radiation, ultrasounds or electric current.

8. Process according to claim 7, where the mild reducer is electric current (electrochemical reduction).

9. Process according to claim 6, where the concentration of reagents is less than $10^{-3}$ M.

10. Process according to claim 9, where in order to maintain the reagent concentration the reaction medium comprises single-phase or two-phase media.

11. Process according to claim 10, where the two-phase systems are formed by water, wherein the metal salt is dissolved in, and an organic compound, where the reducer is dissolved in.

12. Process according to claim 11, where the organic compounds are selected from the group which comprises cyclic, linear or branched saturated and unsaturated hydrocarbons, as well as benzene or toluene.

13. Process according to claim 10, which comprises a detergent in addition to water and an organic compound.

14. Process according to claim 13, where the detergent is chosen from the group which comprises anionic, cationic or non-ionic detergents.

15. Process according to claim 5 which includes the separation of the AQCs synthesized by their selective precipitation, once the desired size of cluster is reached.

16. A method of electro catalyzing oxygen reduction comprising introducing the AQCs of claim 1 into solution comprising O2.

17. A method of treating breast cancer comprising contacting breast cancer cells with the AQCs of claim 1.

* * * * *